United States Patent
Kurihara et al.

(10) Patent No.: US 11,395,772 B2
(45) Date of Patent: Jul. 26, 2022

(54) ABSORBENT ARTICLE

(71) Applicant: DAIO PAPER CORPORATION, Ehime (JP)

(72) Inventors: Ryoko Kurihara, Tochigi (JP); Junta Tagomori, Tochigi (JP); Mariko Nagashima, Tochigi (JP)

(73) Assignee: DAIO PAPER CORPORATION, Ehime (JP)

(\*) Notice: Subject to any disclaimer, the term of this patent is extended or adjusted under 35 U.S.C. 154(b) by 979 days.

(21) Appl. No.: 16/087,339

(22) PCT Filed: Mar. 24, 2017

(86) PCT No.: PCT/JP2017/012003
§ 371 (c)(1),
(2) Date: Sep. 21, 2018

(87) PCT Pub. No.: WO2017/164367
PCT Pub. Date: Sep. 28, 2017

(65) Prior Publication Data
US 2021/0205154 A1    Jul. 8, 2021

(30) Foreign Application Priority Data
Mar. 24, 2016  (JP) .............................. JP2016-060580

(51) Int. Cl.
*A61F 13/511*    (2006.01)
*A61F 13/47*     (2006.01)
(Continued)

(52) U.S. Cl.
CPC ........ *A61F 13/51104* (2013.01); *A61F 13/47* (2013.01); *A61F 13/5123* (2013.01);
(Continued)

(58) Field of Classification Search
CPC ................. A61F 13/47; A61F 13/51104; A61F 13/51108; A61F 13/51113; A61F 13/5116;
(Continued)

(56) References Cited

U.S. PATENT DOCUMENTS 3,881,487 A * 5/1975 Schrading ............. A61F 13/539
604/374
4,892,535 A * 1/1990 Bjornberg ............. A61F 13/515
604/366

(Continued)

FOREIGN PATENT DOCUMENTS

JP    2004-345357    12/2004
JP    2009-148328     7/2009
(Continued)

OTHER PUBLICATIONS

Machine Translation of JP 2010-269029 A (Year: 2010).*
International Search Report dated Jun. 27, 2017 in International (PCT) Application No. PCT/JP2017/012003.

*Primary Examiner* — Catharine L Anderson
(74) *Attorney, Agent, or Firm* — Wenderoth, Lind & Ponack, L.L.P.

(57) ABSTRACT

An objective is to provide an absorbent article that can prevent backflow and can reduce water retention in a front sheet as much as possible. In an incontinence pad 1 for use with a medium or larger volume that absorbs 20 cc or a larger volume of urine, a front sheet 3 is formed by coating a water repellent on a spunlace nonwoven fabric that is made of 100 wt. % of cotton fiber. On a skin facing surface side, in a plan view, recess part lines 20, 21 of a diamond-shaped lattice pattern are formed from many first recess part lines 20 that go along a predetermined inclination angle direction and are formed with a constant gap in the pad longitudinal direction and many second recess part lines 21 that go along the inclination angle direction obtained by reversing the first (Continued)

recess part lines 20 in a width direction by the pad longitudinal direction and are formed with a constant gap in the pad longitudinal direction, partition areas 22 of a diamond-shaped lattice shape partitioned by these recess part lines 20, 21 are arranged adjacently in the longitudinal direction and the width direction. Furthermore, many open holes 10 penetrating through both sides are formed at least at an excretion hole corresponding part H.

8 Claims, 5 Drawing Sheets

(51) Int. Cl.
  *A61F 13/512* (2006.01)
  *A61L 15/20* (2006.01)
  *A61L 15/52* (2006.01)
  *A61F 13/51* (2006.01)
  *A61F 13/53* (2006.01)
(52) U.S. Cl.
  CPC ............... *A61L 15/20* (2013.01); *A61L 15/52* (2013.01); *A61F 2013/51019* (2013.01); *A61F 2013/51026* (2013.01); *A61F 2013/51085* (2013.01); *A61F 2013/53035* (2013.01)
(58) Field of Classification Search
  CPC ........ A61F 13/5123; A61F 2013/51059; A61F 2013/51061; A61F 2013/51078; A61F 2013/5108; A61F 2013/51085; A61F 2013/51165
  See application file for complete search history.

(56) References Cited

U.S. PATENT DOCUMENTS

| | | | |
|---|---|---|---|
| 5,613,960 A * | 3/1997 | Mizutani | A61F 13/53747 604/365 |
| 6,153,209 A * | 11/2000 | Vega | A61L 15/34 424/404 |
| 7,303,808 B2 * | 12/2007 | Taneichi | A61F 13/494 428/114 |
| 2015/0250917 A1 * | 9/2015 | Wada | A61L 15/34 604/367 |

FOREIGN PATENT DOCUMENTS

| | | | |
|---|---|---|---|
| JP | 2010-269029 | | 12/2010 |
| JP | 2010269029 A | * | 12/2010 |
| JP | 2011-200446 | | 10/2011 |
| JP | 2015-100574 | | 6/2015 |
| WO | 2011/155284 | | 12/2011 |

* cited by examiner

[Fig. 1]
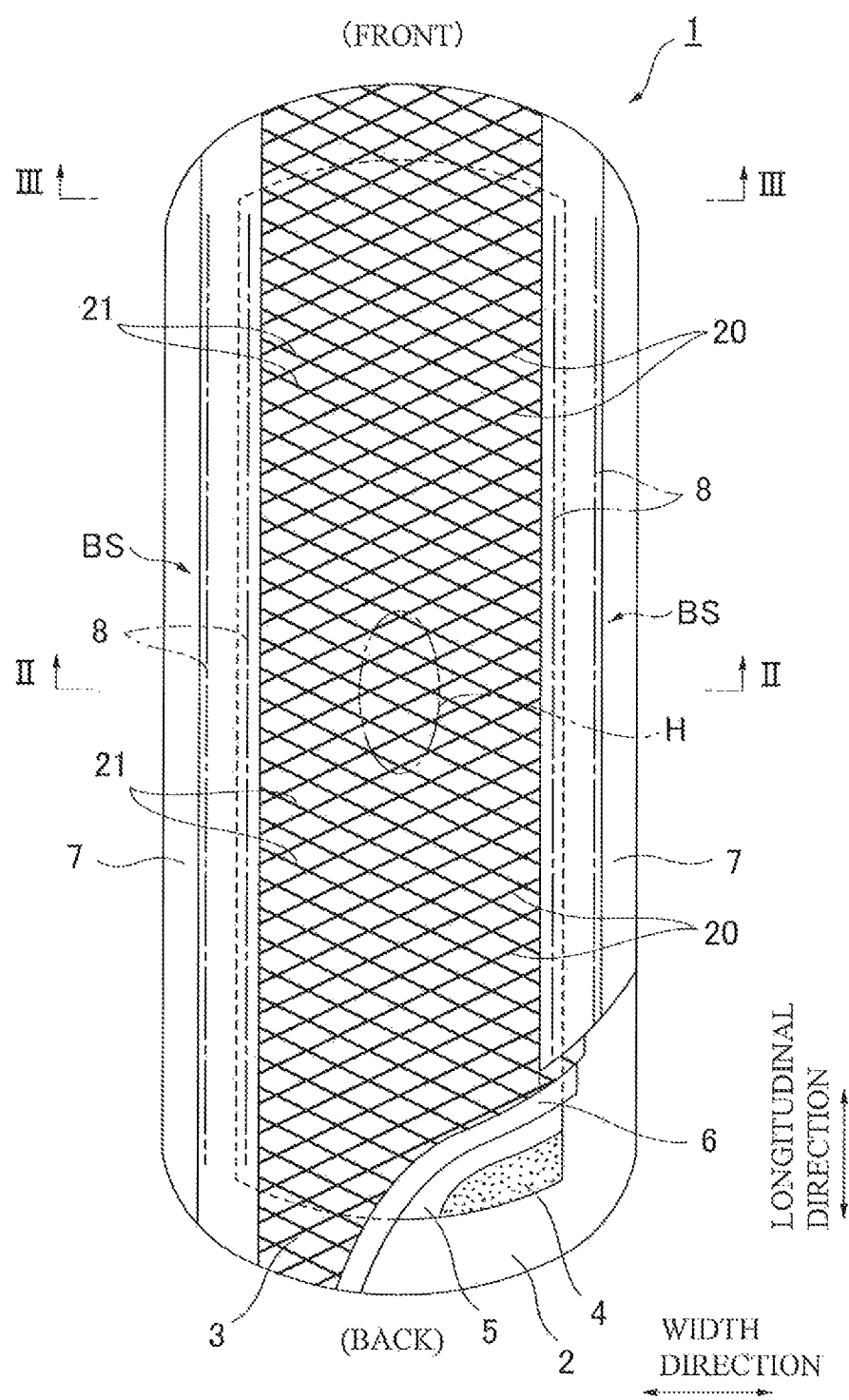

[Fig. 2]
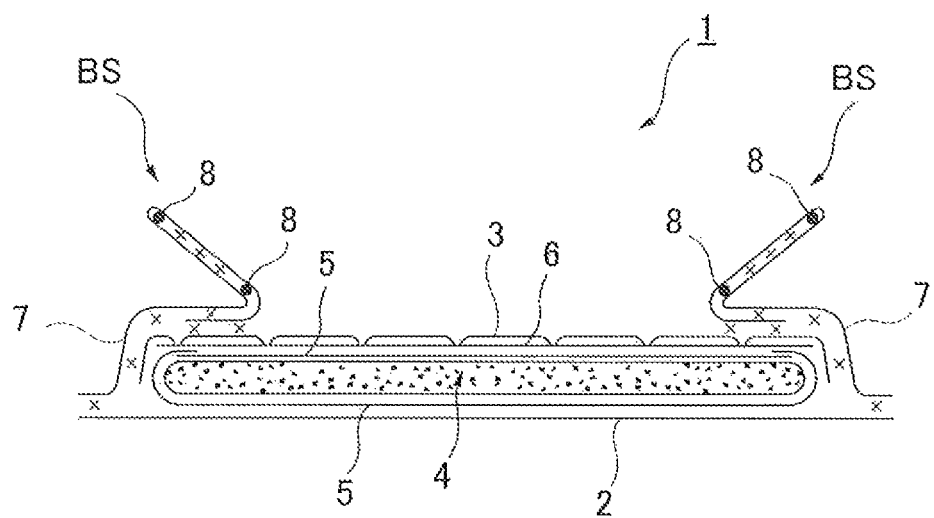
[Fig. 3]
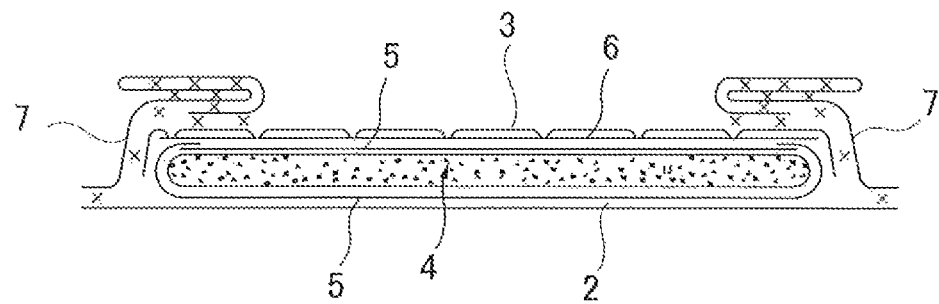

[Fig. 4]
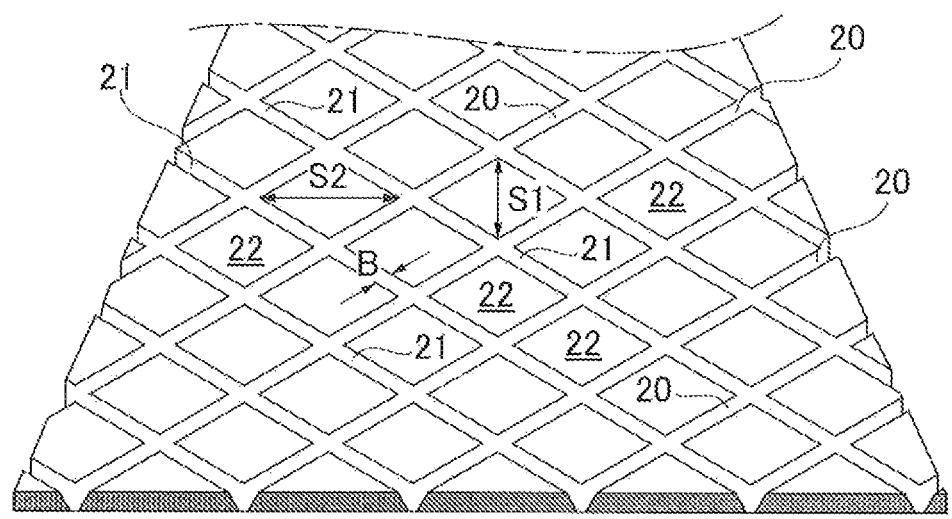
[Fig. 5]
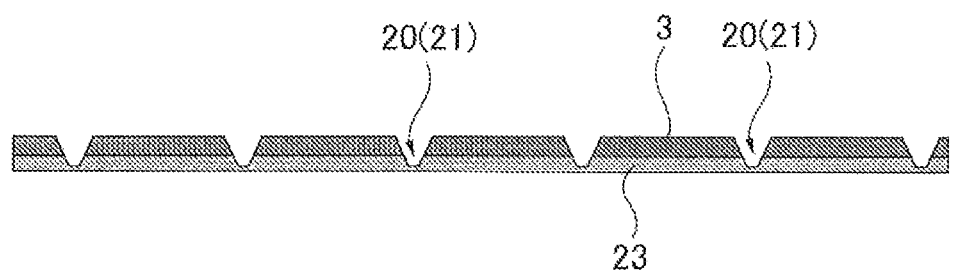

[Fig. 6]
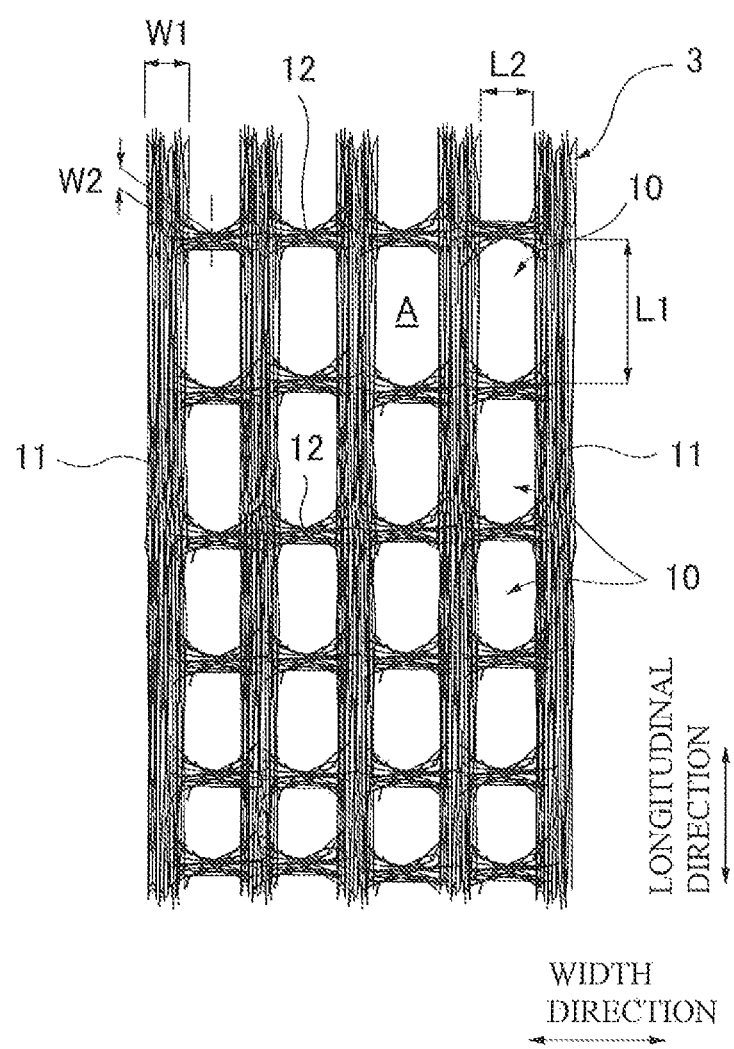

[Fig. 7]
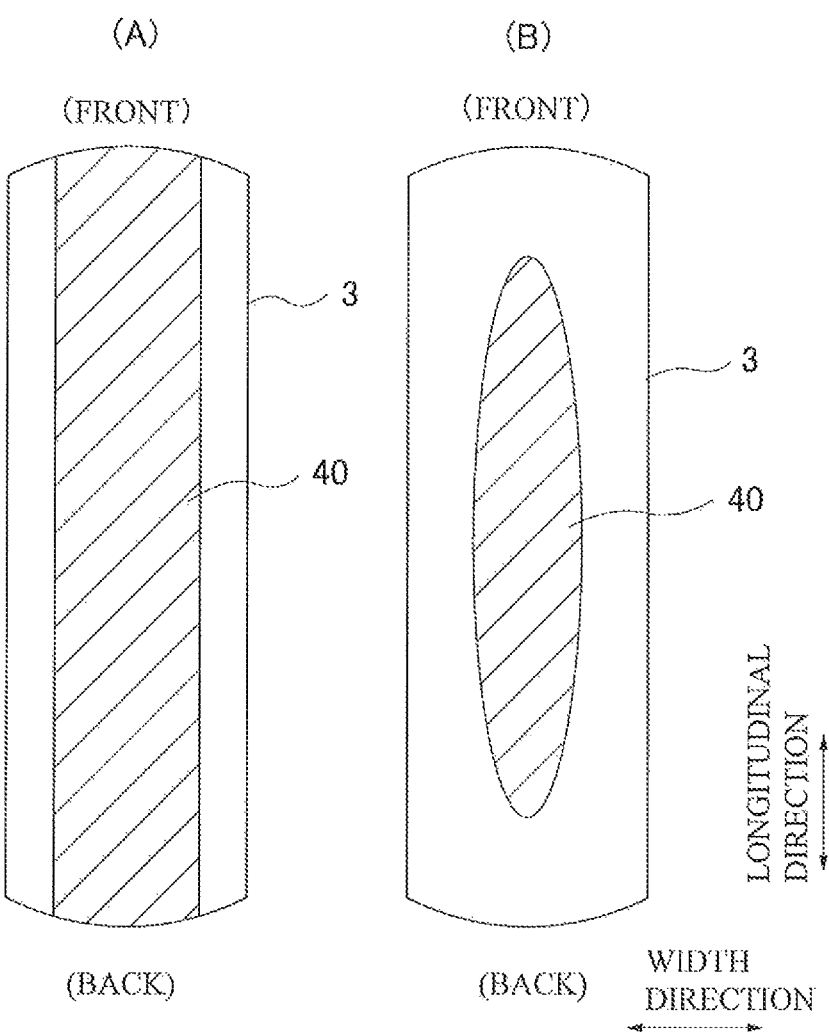

ABSORBENT ARTICLE

TECHNICAL FIELD

The present invention relates mainly to an absorbent article that is used for incontinence pads, in particular, to an absorbent article having a front sheet made of 100 wt. % of cotton fiber and having irregularities formed on a skin facing surface side.

BACKGROUND ART

So far, as absorbent articles for women such as incontinence pads, panty liners (vaginal discharge sheets), and sanitary napkins, ones in which an absorber made of paper cotton such as pulverized pulp or the like is interposed between a liquid-impermeable back sheet such as a polyethylene sheet or a polyethylene sheet laminate nonwoven fabric and a front sheet are known.

Since the front sheet forms a skin contact surface, it is required to be soft, to be able to obtain a dry skin feeling even after absorption of an excreted liquid, to have less irritation to the skin, and the like. As raw materials that satisfy requirements like this, nonwoven fabrics of synthetic fiber, and resinous mesh sheets are broadly adopted in the field of absorbent articles, particularly in the field of incontinence pads. However, there was a problem that the front sheet made of the synthetic fiber causes itching, rash or the like.

As one that solves this problem, a front sheet having cotton fiber as a raw material has been proposed. However, in absorbent articles, while the front sheet is desired to have high liquid permeability and to make the liquid speedily reach the absorber, when ordinary degreased cotton fiber was contained in the front sheet, there was a problem that the front sheet itself has high liquid retention and a sticky feeling tends to remain on a surface.

Furthermore, while an absorbent article having a front sheet made of cotton fiber has an advantage in being able to realize a soft feeling like underwear, when a large volume of body fluid is excreted, since the liquid retention is high as was described above, the body fluid remains in the front sheet, and when wearing for a long time, a sweaty feeling or rash may be caused. Therefore, in the conventional absorbent articles, when the cotton fiber is used in the front sheet, its use was limited to products in which an absorption volume of the body fluid is slight like in vaginal discharge sheets.

As absorbent articles that use a cotton fiber in the front sheet like this, the following Patent Literatures 1 and 2 can be cited. In the Patent Literature 1 below, an absorbent article is disclosed in which a front sheet is constituted of cotton nonwoven fabric, and on a lower layer of the front sheet and between an absorber, a hot melt fiber sheet having lower fiber density than the cotton nonwoven fabric and hydrophilicity is interposed, and, in a laminate state of these, many embossing patterns are formed from a front side.

Furthermore, in the Patent Literature 2, an absorbent article is disclosed in which a top sheet is made of a spunlace nonwoven fabric made of 40 to 100 wt. % of cotton fiber and 60 to 0 wt. % of synthetic fiber which is coated with a water repellent, a skin contact surface has water absorbency of 0 mm to 5 mm, and at least at an excretion hole part, many openings that penetrate through two sides are formed. According to such an absorbent article, due to adoption of the spunlace nonwoven fabric having high cotton fiber content as the top sheet, many advantages of the cotton fiber such as excellent skin contact, difficulty in causing itching, rash, or the like may be obtained. Furthermore, a liquid residue on a front surface that becomes a problem at this time is sufficiently improved by securing water absorbency of the skin contact surface at a sufficiently low level due to the coating (external addition) of the water repellent. However, since merely making the water absorbency low results in a liquid part of the excreted matter going through the top sheet with difficulty, causing lateral leakage or the like, in the absorbent article described in the Patent Literature 1, at least in the excretion hole part in the top sheet, many openings that go through two sides are provided to make it possible to speedily absorb the liquid. As a result thereof, in the Patent Literature 1, advantages such as the stickiness due to liquid residue on a front surface is able to be sufficiently prevented, and excreted liquid once absorbed returns to a front surface side of the top sheet with difficulty, due to the water repellency of the top sheet, are described.

PRIOR ART LITERATURE

Patent Literature

Patent Literature 1: JP 2009-148328 A
Patent Literature 2: JP 2010-269029 A

SUMMARY OF THE INVENTION

Problem to be Solved by the Invention

However, when urine of a medium volume or more, a total volume of 20 cc or more, is absorbed, in the absorbent articles described in the Patent Literatures 1 and 2, the front sheet may retain water, and it was necessary to devise an article that prevents the front sheet from retaining water for as long as possible.

Furthermore, since the absorbent articles are formed in a long and narrow shape in the longitudinal direction, it was demanded to prevent the lateral leakage by promoting diffusion of the urine in the longitudinal direction of the absorbent article.

Furthermore, in the absorbent articles described in the Patent Literatures 1 and 2, since a skin contact surface of the front sheet is formed substantially flat, when the cotton fiber is used as the front sheet, the sticky feeling due to the front sheet retaining water tends to be readily felt, itching, rash, or the like are caused, and a sufficient cushioning property was difficult to obtain.

In light of this, a primary problem of the present invention is to provide, in an absorbent article that use cotton fiber in the front sheet, an absorbent article in which the liquid retention of the front sheet is reduced as much as possible, the liquid tends to diffuse in the longitudinal direction, and an excellent cushioning property is imparted.

Means for Solving the Problem

As the present invention relating to claim 1 for solving the problem, in an absorbent article in which an absorber is interposed between a front sheet and a back sheet:

the absorbent article is an incontinence pad for use with a medium or larger volume that absorbs 20 cc or a larger volume of urine;

in which the front sheet is formed by coating a water repellent on a spunlace nonwoven fabric made of 100 wt. % of cotton fiber coated with a water repellent and, on a skin facing surface side thereof, in a plan view, recess part lines of a diamond-shaped lattice pattern are formed from many first recess part lines that go along a predetermined inclination angle direction and are formed with a constant gap in the longitudinal direction of the absorbent article and many second recess part lines that go along an inclination angle direction obtained by reversing the first recess part lines in a width direction by the longitudinal direction of the absorbent article and are formed with a constant gap in the longitudinal direction of the absorbent article, partition areas of a diamond-shaped lattice shape partitioned by these recess part lines are arranged adjacently in the longitudinal direction and the width direction of the absorbent article, and many open holes penetrating through two sides are formed at least at an excretion hole corresponding part, and on the absorber side of the front sheet, a second sheet made of a thermoplastic fiber is adhered thereto, and at the same time, the front sheet and the second sheet are bonded at the first recess part lines and second recess part lines by heat sealing of the second sheet, basis weights of the recess part lines and a basis weight of the partition area are formed at a substantially equal level, and the density of the recess part lines is formed higher than the density of the partition area.

In the invention according to claim 1, incontinence pads for use with a medium or larger volume that absorbs urine from abdominal pressure urinary incontinence that is instantaneously excreted when force, such as a cough, sneeze, or when holding a heavy object, is applied to an abdominal part or when a heavy object is held, or from impending incontinence in which a person is struck by a sudden urge to urinate and excretes in one go, incapable of suppression thereof, and that absorbs a total urinary volume of 20 cc or more are targeted. It is to be noted that, in many cases, the incontinence pad is continuously used until a second incontinence, that is, it is worn for a long time in a state after the first incontinence, and is discarded after a second urination.

Furthermore, in the present absorbent article, as the front sheet, one is used in which a water repellent is coated on a spunlace nonwoven fabric made of 100 wt. % of cotton fiber, and, on a skin facing surface side, in a plan view, recess part lines of a diamond-shaped lattice pattern are formed from many first recess part lines that go along a predetermined inclination angle direction and are formed with a predetermined gap in the longitudinal direction of the absorbent article and many second recess part lines that go along an inclination angle direction obtained by reversing the first recess part lines in a width direction by the longitudinal direction of the absorbent article and formed at a constant gap in the longitudinal direction of the absorbent article, and partition areas of the diamond-shaped lattice shape partitioned by these recess part lines are arranged adjacently in the longitudinal and width directions of the absorbent article. Accordingly, due to adoption of the spunlace nonwoven fabric made of 100 mass % of the cotton fiber, a soft skin feeling is obtained, and skin trouble during wearing such as itching or rash is made difficult to occur even when wearing for a long time. The retained water of the front sheet that becomes a problem at this time is eliminated by coating a water repellent at least on an excretion hole corresponding part and forming recess part lines of a diamond-shaped lattice pattern on a skin facing surface side to promote diffusion of the excreted liquid, thereby reducing the volume of excreted liquid that permeates per unit area.

Furthermore, since, in the front sheet, the body fluid having flowed along the recess part lines tends to pass a bottom part of the recess part lines to move to an absorber side on a lower layer, and many open holes that go through the both sides are formed at least in the excretion hole corresponding part of the front sheet, urine tends to pass through the front sheet through the open holes so as to reduce an amount of water retention in the front sheet.

Furthermore, since the skin facing surface side of the front sheet is formed in an irregular shape, the compression restoring force of the front sheet becomes higher, the cushioning property becomes excellent, and an irregular shape on the skin facing surface side tends to be readily maintained.

Furthermore, in the invention described in the claim 1, a second sheet made of a thermoplastic fiber is adhered to an absorber side of the front sheet, and, due to the crushing from the front side of the front sheet, the front sheet and the second sheet are bonded at the recess part lines by heat sealing of the second sheet. Since the front sheet is made of the cotton fiber, it is difficult to retain recess grooves due to the crushing. However, when crushing together with the second sheet made of the thermoplastic fiber, since molten thermoplastic fiber penetrates in the front sheet to fuse, a crushed state of the front sheet is held. Thus, the basis weight of the recess part and the basis weight of the protruded part are formed at substantially the same level and the density of the recess part is formed higher than the density of the protruded part. Therefore, the body fluid absorbed by the front sheet is attracted to the recess part having high density from the protruded part having low density by a capillary action due to a density gradient of the fiber, body fluid transfer from the recess part to the absorber side is promoted, and the amount of water retention in the protruded part contacting with the skin surface decreases.

As the present invention according to claim 2, the absorbent article according to claim 1, in which the first recess part lines and second recess part lines are formed by any one of a continuous line or an intermittent line, is provided.

In the invention described in the claim 2, a line aspect of the first recess part lines and second recess part lines is defined. Specifically, the recess part lines may be formed by a continuous line or an intermittent line.

As an invention according to claim 3, the absorbent article according to any one of claims 1 and 2, in which as the water repellent, glyceryl stearate is used, is provided.

In the invention described in the claim 3, due to the use of glyceryl stearate as the water repellent, urine is not absorbed by the cotton fiber of the front sheet but is made to flow easily to the absorber side.

As the present invention according to claim 4, the absorbent article described in any one of claims 1 to 3, in which the front sheet is made of degreased cotton fiber or non-degreased cotton fiber, is provided.

In the invention described in the claim 4, as the front sheet, either of the degreased cotton fiber and non-degreased cotton fiber may be used. When the non-degreased cotton fiber is used, since the amount of water retention in the front sheet may be further reduced, the liquid residue in the front sheet becomes difficult to occur.

Effect of the Invention

As was detailed in the above, according to the present invention, in the absorbent article that uses cotton fiber in the front sheet, the water retention in the front sheet can be reduced as much as possible, the liquid dispersion tends to occur in the longitudinal direction, and the cushioning property can be excellent.

BRIEF DESCRIPTION OF THE DRAWINGS

FIG. 1 is a partially broken development view of an incontinence pad 1 according to the present invention.

FIG. 2 is an arrow view taken along a II-II line of FIG. 1.

FIG. 3 is an arrow view taken along a line of FIG. 1.

FIG. 4 is an enlarged perspective view of an essential part of a front sheet 3.

FIG. 5 is a lamination cross-sectional view between the front sheet 3 and a second sheet 23.

FIG. 6 is an enlarged plan view when an open hole is formed in the front sheet 3.

FIG. 7 is a development view showing a water repellent coating pattern of the front sheet 3.

MODES FOR CARRYING OUT THE INVENTION

In what follows, an embodiment of the present invention will be detailed with reference to the drawings.

The present invention is an incontinence pad 1 for use with a medium or larger volume suitable for absorbing 20 cc or a larger volume of urine in total, and is particularly suitable for absorbing urine from abdominal pressure urinary incontinence that is instantaneously excreted when force, such as a sneeze, cough, or when holding a heavy object, is applied to an abdominal part or when a heavy object is held, or from impending incontinence in which a person is struck by a sudden urge to urinate and excretes in one go, incapable of suppression thereof.

(One Example of Basic Structure of Incontinence Pad)

An incontinence pad 1 according to the present invention is constituted mainly of, as shown in FIGS. 1 to 3: a liquid-impermeable back sheet 2 made of a polyethylene sheet or the like; a front sheet 3 that forms a skin contact surface and allows rapid passage of urine or the like; an absorber 4 interposed between these two sheets 2 and 3 and made of cotton pulp or synthetic pulp; and a pair of right and left three-dimensional gathers BS and BS provided in a protruded state on a skin side in a predetermined interval in the front-back direction with a substantial side edge part of the absorber 4 as a rise-up base edge so as to contain at least a urination hole part H of a wearer, and in which in the surrounding of the absorber 4, at upper and lower end edge parts thereof, outer edge parts of the liquid-impermeable back sheet 2 and front sheet 3 are joined by adhering means such as an adhesive including hot melt or heat seal, furthermore, at both lateral edge parts thereof, the liquid-impermeable back sheet 2 that extends further to the lateral side than the absorber 4 and a side non-woven fabric 7 that forms the three-dimensional gather BS are joined by adhering means such as an adhesive agent including hot melt or heat seal. In an illustrated example, the absorber 4 is formed into one layer structure but may be formed into a multi-layered structure that forms a center high part, and furthermore, may be formed into a multi-layered structure in which absorbers having the same size and shape are stacked.

In the liquid-impermeable back sheet 2, although a sheet material having at least a water-blocking property such as polyethylene is used, in recent years, from the viewpoint of preventing a sweaty feeling, a material having moisture permeability tends to be used. As the water-blocking and moisture-permeable sheet material, a microporous sheet that is obtained by molding a sheet by melting and kneading an inorganic filler in an olefin-based resin such as polyethylene or polypropylene, followed by stretching in one or a biaxial direction is suitably used. On a non-used surface side (outside surface) of the liquid-impermeable back sheet 2, one or a plurality of stripes of adhesive layers (not shown in the drawing) are formed, and the incontinence pad 1 is fixed to underwear when wearing on the body. As the liquid-impermeable back sheet 2, a polylaminated nonwoven fabric obtained by laminating a plastic film and a nonwoven fabric may be used.

In the illustrated example, the front sheet 3 is formed to an extent of having a width slightly larger than a width of the absorber 4 and covers only the absorber 4, the outside in the width direction of the front sheet 3 is covered with the side nonwoven fabric 7 (a member separate from the front sheet 3) that extends from surfaces of both side parts of the front sheet 3. A part on a center side in the width direction of the side nonwoven fabric 7 forms a three-dimensional gather BS. As the side nonwoven fabric 7, responding to objects such as preventing the penetration of urine or enhancing the skin contact feeling, a nonwoven fabric material to which appropriate water repelling treatment or hydrophilic treatment is applied may be used. As such side nonwoven fabric 7, one formed according to an appropriate processing method with a natural fiber, a synthetic fiber or a recycled fiber as a raw material may be used. However, preferably, in order to eliminate a stiff feeling and to prevent the sweaty feeling, a nonwoven fabric of which basis weight is suppressed to give an aeration property may be used. Specifically, a nonwoven fabric produced by setting the basis weight to 15 to 23 $g/m^2$ is desirably used, and in order to surely prevent passage of the body fluid, a nonwoven fabric, to which the water repelling treatment is applied by coating a water repellent that is for example silicon-based or paraffin-based, may be suitably used.

The side nonwoven fabric 7 adheres, as shown in FIG. 2 and FIG. 3, with an adhesive such as hot-melt at a portion further outside than an intermediate part in a width direction over a range from an inside position of the absorber 4 to an outside edge of the liquid-impermeable back sheet 2 exceeding an absorber side edge by a little.

On the other hand, an inner side portion of the side nonwoven fabric 7 is folded into substantially two fold, and, in the inside of the twofold sheet, one or a plurality of, in the illustrated example, two thread-like elastic stretchable members 8 and 8 of which both ends or appropriate positions in the longitudinal direction are fixed at the intermediate part in the height direction are provided in a state where both ends or an appropriate position in the longitudinal direction are fixed. This twofold sheet part is, in the front-back end parts, fixed on the front sheet 3 side in a folded state as shown in FIG. 3.

(Front Sheet)

The front sheet 3 forms a skin contact surface that is a part covering a skin side of the absorber 4 and is constituted of a spunlace nonwoven fabric made of 100 wt. % of cotton fiber. The spunlace nonwoven fabric has advantageous points such as that it does not use an adhesive and that it has flexibility.

The nonwoven fabric of the front sheet 3 is used in the cotton fiber alone and does not contain a synthetic fiber. As the cotton fiber, although all cotton fibers such as raw cotton of cotton, refined/bleached cotton fiber or dyed cotton fiber after refining and bleaching, refined/bleached degreased cotton fiber, further, recovered wool obtained by fibrillating one that was formed into thread or cloth or the like can be used, in particular, non-degreased cotton provided with a slight water repellency even in a fibrous state due to natural fat of cotton wax adhered to a surface of the cotton fiber is preferably used.

In the front sheet 3, as shown also in FIG. 4, on the skin facing surface side, in a plan view, recess part lines 20 . . . , 21 . . . of a diamond-shaped lattice pattern are formed from many first recess part lines 20, 20 . . . formed along a predetermined inclination angle direction and with a constant gap in the longitudinal direction of the incontinence pad 1, and many second recess part lines 21, 21 . . . formed along an inclination angle direction obtained by reversing the first recess part lines 20, 20 . . . in the width direction by the longitudinal direction line of the incontinence pad 1 and are formed with a constant gap in the longitudinal direction of the incontinence pad 1, and partition areas 22, 22 . . . of a diamond lattice shape partitioned by these recess part lines 20 . . . , 21 . . . are arranged adjacently in the longitudinal width directions of the incontinence pad 1.

The front sheet 3 has single-layer or multi-layered nonwoven fabric structure. A non-skin facing surface side (absorber 4 side) is formed substantially flat, and almost the entire surface makes contact with a member arranged on the absorber 4 side, whereby the body fluid absorbed by the front sheet 3 tends to move to the absorber 4.

Cross-sectional shapes of the first recess part lines 20 and second recess part lines 21 formed on the skin facing surface side of the front sheet 3 substantially have a reversed triangle shape. That is, a width on a front side is relatively wide, and the width becomes progressively narrower going toward a bottom part side. An inclined surface may be a straight line, or an arc swelling to a groove side. Further, the first recess part lines 20 and second recess part lines 21 are formed into a so-called "line shape" but this may be a continuous line, or an intermittent line with a crushed part and a non-crushed part alternately provided. When forming the intermittent line, it is desirable to avoid disturbing the flow of the body fluid, by preventing swelling of the non-crushed part by making a length of the non-crushed part 3 mm or shorter, preferably 1.5 mm or shorter.

The partition area 22 surrounded by the recess part lines 20 . . . , 21 . . . maintains an initial thickness of the nonwoven fabric and is formed into a flat shape.

Widths B of the recess part lines 20, 21 are desirably formed at the same width, 0.2 to 2.0 mm, preferably 0.3 to 1.0 mm. Furthermore, a longitudinal dimension S1 and a transversal dimension S2 of the partition area 22 are set desirably at 5 to 20 mm, and preferably at 6 to 15 mm. Regarding a shape of the partition area 22, in the case where a diamond-shaped shape is formed longer in the width direction with the transversal dimension S2>the longitudinal dimension S1, when receiving leg pressure from both side parts, deformation resistance force with respect to the width direction becomes higher, and twists or creases along the longitudinal direction become difficult to occur. Furthermore, in the case where the diamond-shaped shape is formed longer in the longitudinal direction with the transversal dimension S2<the longitudinal dimension S1, the deformation resistance force in the front-back direction becomes higher, and twists or creases along the width direction become difficult to occur.

As will be described below, the front sheet 3 is produced by imparting embossing along the first recess part lines 20, 20 . . . and the second recess part lines 21, 21 . . . , the basis weight of the recess part lines 21, 21 . . . and the basis weight of the partition area 22 are formed at substantially the same level, and the density of the recess part lines 21, 21 . . . is formed higher than the density of the partition area 22. Therefore, although the body fluid absorbed by the front sheet 3 permeates to the lower side as it is in the center part of the partition area 22 and is absorbed by the absorber 4, the body fluid excreted to an area close to the recess part lines 20, 21 is attracted to the recess part lines 20 . . . , 21 . . . side having high density from the partition area 22 having low density by a capillary action due to the density gradient of the fiber, body fluid transfer from the recess part lines 20 . . . , 21 . . . to the absorber side is promoted, and the amount of water retention in the partition area 22 in contact with a skin surface decreases.

A thickness of the partition area 22 is set at 0.25 to 2 mm, preferably at 0.3 to 0.8 mm, and a thickness of the recess part lines 20 . . . , 21 . . . is set at 0.1 to 0.5 mm, preferably at 0.15 to 0.3 mm. The thicknesses are obtained according to JIS-L1913.

The front sheet 3 is constituted with a spunlace nonwoven fabric made of 100 wt. % of cotton fiber. Due to the adoption of the spunlace nonwoven fabric made of 100 wt. % of cotton fiber, soft skin feeling is obtained, and the skin trouble during wearing for a long time such as the itching or rash is made difficult to occur. The water retention in the front sheet 3 that is a problem at this time is eliminated by reducing the volume of the excreted liquid passing through per unit area by promoting vertical diffusion of the excreted liquid along the recess part lines 20 . . . , 21 . . . by forming the recess part lines 20 . . . , 21 . . . of the diamond-shaped lattice shape on the skin facing surface side of the incontinence pad 1 on the skin facing surface side of the front sheet 3.

Furthermore, since the skin facing surface side of the front sheet 3 is formed in an irregular shape, the compression restoring force of the front sheet 3 becomes high, the cushioning property becomes excellent, and the irregular shape on the skin facing surface side tends to be readily maintained.

The average basis weight of the front sheet 3 as a whole is 20 to 40 $g/m^2$, preferably 27 to 34 $g/m^2$, more preferably 29 to 32 $g/m^2$. The basis weight is calculated in terms of square meter after measuring a weight of 5 cm×30 cm×10 sheets with an electronic balance.

When producing the front sheet 3 having an irregular shape, since the front sheet 3 is a cotton single layer made of only cotton fiber and does not contain a thermoplastic fiber, a shape of a recess groove due to crushing is difficult to be maintained. Accordingly, by crushing together with the second sheet made of the thermoplastic fiber, molten thermoplastic fiber penetrates into the front sheet to fuse, and a state where the front sheet is crushed can be maintained.

Accordingly, it is desirable to produce the front sheet 3 having an irregular shape in such a manner that, as shown in FIG. 5, on one surface side (a surface side (non-skin facing surface side) of the front sheet 3 facing the absorber 4) of a sheet-like cotton nonwoven fabric made of cotton fiber and having a flat surface, the second sheet 23 made of the thermoplastic fiber is adhered with a hot-melt adhesive or the like, and the laminate sheet is passed between an embossing roll provided with an emboss protrusion part having a diamond-shaped lattice protruding outside on a periphery and an anvil roll having a flat surface, whereby, simultaneously, crushed grooves are formed from a front side of the cotton nonwoven fabric and the cotton nonwoven fabric and the second sheet 23 are joined by heat sealing of the second sheet 23.

In the front sheet 3 produced according to this method, the basis weight of the recess part lines 20 . . . , 21 . . . and the basis weight of the partition area 22 are formed at substantially the same level, and the density of the recess part lines 20 . . . , 21 . . . is formed higher than the density of the partition area 22. Therefore, the body fluid absorbed in the partition area 22 is attracted to the recess part lines 20 . . . , 21 . . . having higher fiber density by the capillary action due to the density gradient of the fiber, the volume of water retained in the partition area 22 adjacent to the skin surface decreases, and the sticky feeling does not occur.

The basis weight of the front sheet 3 at this time is set at the above average basis weight 20 to 40 g/m², preferably at 27 to 34 g/m², and more preferably at 29 to 32 g/m².

Furthermore, the density of the partition area 22 is set at 0.001 to 0.30 g/cm³, preferably at 0.001 to 0.20 g/cm³, and the density of the recess part lines 20 . . . , 21 . . . is set at 0.01 to 3.0 g/cm³, and preferably at 0.1 to 1.0 g/cm³.

In the present production method, the first recess part lines 20 and second recess part lines 21 provided to the front sheet 3 may be formed as a continuous crushed groove or an intermittently crushed groove in which the crushed part and the non-crushed part are alternately repeated.

In the present production method, as the second sheet 23 joined to the front sheet 3, in order to impart a fluffy feeling, a cushioning feeling to the front sheet 3, one having the basis weight of about 10 to 200 g/m², preferably about 20 to 100 g/m² is preferably used. As a raw material of the second sheet 23, one with a thermoplastic property is sufficient, but one having hydrophilicity is particularly preferred. When the second sheet 23 having the thermoplasticity and hydrophilicity like this is combined with a water repellent holed front sheet of the present invention, the irregularity of the front sheet 3 is maintained and the liquid permeability and backflow prevention properties of the front sheet 3 are improved. As the raw material like this, fiber provided with the hydrophilicity by surface treating synthetic fiber that is for example olefin-based such as polyethylene or polypropylene, polyester-based, polyamide-based, or composite fibers thereof, copolymers thereof, or blend bodies thereof with a hydrophilizing agent may be used. Preferably, fiber obtained by mixing polyethylene and polypropylene may be used. As the fiber constituting the nonwoven fabric, any of long fiber, short fiber or mixtures thereof may be used. The fineness is set at about 2.0 to 7.0 dtex, preferably at about 4.0 to 6.0 dtex. As the second sheet 23, any of known forms of nonwoven fabrics such as an air through nonwoven fabric, an air laid nonwoven fabric, and a spun bond nonwoven fabric may be used, but the air through nonwoven fabric that does not deteriorate the air permeability is preferably used.

The first recess part lines 20, 20 . . . and second recess part lines 21, 21 . . . are desirably formed over an entire surface of the front sheet 3, but may be partially formed such as by being formed along the longitudinal direction in a center area portion in the width direction or being formed in a circular or elliptical area containing an excretion part.

Now, in the front sheet 3, as shown in FIG. 6, in order to increase the permeability, at least in the excretion hole corresponding part H, many open holes 10, 10 . . . penetrating through the both sides are preferably provided. Specifically, the open holes 10 may be formed by making the fiber material be carried on a mesh-like support in a hydroentanglement process during spunlace production. In this case, by changing conditions of the mesh used, the individual sizes of open holes and the ratio of open holes can be adjusted. Of course, the open holes may be formed by carrying out a punching process on the nonwoven fabric after production. The open holes 10 may be provided on the entire front sheet but may be provided at least on the excretion hole corresponding part H. Preferably, the open holes are provided on a region that includes the excretion hole corresponding part H, is 15% or more of an absorber length in a product length direction, and is 50% or more of an absorber width in a product width direction, and further preferably, in a region that includes the excretion hole corresponding part H, is 50% or more of the absorber length in the product length direction, and is 70% or more of the absorber width in the product width direction. When an area where the open holes are formed is shorter than 15% of the absorber length in the product length direction and narrower than 50% of the absorber width in the product width direction, there occurs a situation where the incontinence range may not be covered, urine remains in the front sheet 3 to cause a sticky feeling, and the skin trouble during wearing such as itching or rash tends to occur.

When as the front sheet 3, one in which at least on the excretion hole corresponding part H, many open holes 10 that penetrate through the both sides are used, the body fluid rapidly penetrates through the front sheet via the open holes 10, whereby the problem of the liquid residue in the front sheet is decreased.

The open holes 10 are formed, as shown in FIG. 6, in a shape vertically long in the longitudinal direction of the incontinence pad 1. Therefore, since the body fluid tends to pass more easily than in a circular open hole, the urine tends to pass the front sheet 3 via the open holes 10, and the retained water in the front sheet 3 decreases. Further, since when the urine passes the open holes 10, the body fluid goes through while being deformed vertically longer, a diffusion direction of the urine can be controlled in the pad longitudinal direction, the diffusion in the lateral direction is suppressed, and thus, the lateral leakage occurs with more difficulty. It is to be noted that, in the case of the spunlace, the shapes of open holes are difficult to be uniformly formed, however, the shapes of the open holes 10 become shapes that are of roughly rectangular to truncated long holes or elliptical shapes.

As a dimension of the open hole 10, a length L1 in the longitudinal direction of the incontinence pad 1 is set at 1.0 to 4.0 mm, preferably at 1.5 to 3.0 mm, and a length L2 in the width direction of the incontinence pad 1 is set at 0.5 to 1.5 mm, preferably at 0.5 to 1.0 mm. When the dimension of the open hole 10 is shorter than 0.5 mm, the urine is difficult to pass, and a clear open hole is difficult to be formed due to fuzz of the fiber. When a maximum dimension of the open hole 10 exceeds 4.0 mm, the backflow of the liquid from the open hole 10 and surface exposure of the constituent material of the absorber 4 may be caused. Furthermore, a ratio of the L1 and L2 (L1/L2) is set at 1.2 to 5.0, preferably at 2.0 to 3.0. An area A of the open hole 10 is set at 0.9 to 3.0 mm², preferably at 0.9 to 2.5 mm². Furthermore, the ratio of open holes is set at 15 to 45%, preferably at 17 to 30%, and more preferably at 18 to 25%. The dimension of the open hole 10 may not be uniform over an entirety, and may be formed at an arbitrary size as long as the size is within the above range.

The front sheet 3 has a structure in which, as shown in FIG. 6, by the cotton fiber, many vertical lines 11, 11 . . . formed extending along the longitudinal direction of the incontinence pad 1 and distanced in the width direction, and many horizontal lines 12, 12 . . . extending along the width direction of the incontinence pad 1 and connecting between adjacent vertical lines 11, 11 formed distanced in the longitudinal direction are formed, and in a part surrounded by the vertical lines 11 and the horizontal lines 12, the open holes 10 are formed.

A width W1 of the vertical line 11 is set at 0.5 to 2.5 mm, preferably at 0.8 to 2.3 mm. A width W2 of the horizontal line 12 is set at 0.2 to 1.6 mm, preferably at 0.3 to 1.4 mm. Furthermore, a ratio of the W1 and W2 (W1/W2) is set at 1.2 to 2.0, preferably at 1.5 to 2.0. When the width W1 of the vertical line 11 is set larger than the width W2 of the horizontal line 12, the liquid diffusion in the longitudinal direction of the incontinence pad 1 along the vertical line 11 tends to occur.

The vertical lines 11 have a larger fiber amount and a larger density than the horizontal lines 12. Thus, only a part of the vertical line 11 makes contact with the skin, and due to reduction of a contact area with the skin, even when wearing for a long time, the skin trouble during wearing such as itching or rash becomes difficult to occur, and the sticky feeling is reduced after incontinence as well. Furthermore, when the urine passes the front sheet 3, the diffusion in the longitudinal direction of the incontinence pad 1 along the vertical lines 11 of relatively high density tends to occur by the capillary phenomenon of the fiber. Furthermore, since the diffusion directions of the urine passing the open holes 10 and the urine penetrating through the front sheet 3 coincide in the longitudinal direction of the incontinence pad 1, as if being pulled by the urine passing the open hole 10, the urine permeates the vertical lines 11 of the front sheet 3, whereby the liquid residue of the front sheet 3 is suppressed as much as possible.

The fiber amount can be measured according to JIS P8207 "Pulps—Test method for classification with screens". Furthermore, the density may be measured according to JIS P8118 "Paper and board—Determination of thickness, density and specific volume".

In the front sheet 3, a water repellent is externally coated on at least the excretion hole corresponding part H. As the water repellent, among known ones such as paraffin-based, silicone-based or the like, one less irritant to the skin may be appropriately selected and used. However, it is more preferable to appropriately select and use fats and oils less that are less irritant, such as glyceryl stearate, stearic acid amide, zinc stearate, calcium stearate, stearic acid diethanol amide, and magnesium stearate. Among these, glyceryl stearate is particularly preferred. When the water repellent made of glyceryl stearate is used in the incontinence pad 1, its coating amount is preferably set at 0.05 to 0.30 pt. wt. relative to 100 pts. wt. of the fiber (a total coating amount in the case of double-sided coating). A more preferable coating amount is 0.08 to 0.25 pt. wt. When the coating amount of the water repellent is less than 0.05 pt. wt., there may be a case where the water repellent effect is insufficient, and, when the coating amount exceeds 0.30 pt. wt., the water repellency is excessive, resulting in difficulty in passing the moisture.

The water repellent may be coated only on the skin contact face, and may be coated on both surfaces of the skin contact surface and a surface on the absorber 4 side. An amount of water absorption obtained from at least a water amount test described below is set at 0.03 g or lower, and preferably at 0.02 g or lower.

The amount of water absorption in the front sheet 3 is obtained according to the following procedure. (1) A sample of 10 cm square is prepared and its weight is measured (A). (2) Three filter papers of 10 cm square are superposed with a smooth surface side held upward and the sample is set thereon. (3) On the set sample, 3 ml of room temperature tap water is dropped and left for 5 minutes. (4) Weight of the sample left for 5 minutes is measured (B). (5) An amount of water absorption (retained water) in the front sheet 3 is obtained from (B)−(A)=amount of water absorption (g).

In particular, it is preferable that the water absorbency of a surface on the absorber 4 side in the front sheet 3 is higher than the water absorbency of the skin contact surface. Therefore, it is preferable that the water absorbency (JIS L1907 Byreck method) on the skin contact surface side is set at 0 mm to 5 mm, preferably at 0 mm to 2 mm, and the water absorbency (JIS L1907 Byreck method) of a surface on the absorber 4 side is set at 0 mm to 10 mm, in particular at about 2 mm to 4 mm. A difference of the water absorbency like this can be readily obtained by coating the water repellent only on the skin contact surface of the front sheet 3. However, the water repellent may also be coated on both sides of the front sheet 3; in this case, the water repellent is coated on a surface on the absorber 4 side in an amount smaller than that on the skin contact surface. It is to be noted that, even when the water repellent is coated only on the skin contact surface of the front sheet 3, depending on the thickness or the basis weight, the surface on the absorber 4 side also becomes water-repellent. Whether the water repellent is coated only on one side or on both sides, or how a ratio of coating amounts on both sides is set when coating on both sides, is appropriately selected such that, in addition to conditions of the thickness of the front sheet 3, the basis weight, open holes, and the like, a good balance can be maintained with the liquid permeability and moisture absorbency.

As a coating method of the water repellent, well-known methods such as a transfer method, a misting method, a brushing method, a soaking method, or a dipping method can be appropriately used. When a difference in water absorbency between both sides of the sheet is to be provided, a coating method due to transfer may be preferably used.

The water repellent is preferably coated over an entire surface from the viewpoint of production efficiency, but it is sufficient for at least the excretion hole corresponding part H, and the water repellent may be coated only on a part that receives the excreted liquid. For example, as shown in FIG. 7(A), a water repellent coating part 40 may be provided while excluding both side parts in the width direction. Furthermore, as shown in FIG. 7(B), the water repellent coating part 40 may be provided only on a part at a center in the width direction and at an intermediate in the front-back direction.

(Absorber 4)

The absorber 4 can absorb and retain the urine and one in which a particulate superabsorbent polymer is dispersed and mixed in fluffy pulp fiber may be used. The absorber 4 is made of only the pulp fiber and the superabsorbent polymer and does not contain synthetic fiber.

As the pulp fiber, one made of cellulose fiber such as chemical pulp or liquefied pulp obtained from timber, and artificial cellulose fiber such as rayon, acetate can be used, and softwood pulp having a fiber length longer than hardwood pulp is suitably used from the viewpoint of function and price.

The basis weight of the pulp fiber is set at 75 to 300 g/m$^2$, and preferably at 155 to 270 g/m$^2$, and the basis weight of the superabsorbent polymer is set at 85 to 185 g/m$^2$, and preferably at 100 to 165 g/m$^2$.

As the superabsorbent polymer, for example, crosslinked polyacrylate, self-crosslinked polyacrylate, saponified acrylic acid ester-vinyl acetate copolymer crosslinked product, isobutylene/maleic anhydride copolymer crosslinked product, crosslinked polysulfonate, and ones obtained by partially crosslinking water-swelling polymers, such as polyethylene oxide and polyacryl amide, and the like may be used. Among these, ones based on acrylic acid or acrylate having an excellent water absorption amount and water absorption speed are preferable. An absorption magnification (water absorption power) and absorption speed may be adjusted by adjusting a crosslinking density and a crosslinking density gradient in the production process of the superabsorbent polymer having water absorption performance.

A ratio of the pulp fiber and superabsorbent polymer is set at pulp fiber:superabsorbent polymer=70 to 30 wt. %: 30 to 70 wt. %, preferably at 62 to 45 wt. %: 38 to 55 wt. %, and more preferably at 60 to 50 wt. %: 40 to 50 wt. %.

In the present incontinence pad 1, since an absorber in which the pulp fiber and the superabsorbent polymer each is constituted at a predetermined basis weight and the pulp fiber and the superabsorbent polymer each is constituted at a predetermined weight ratio is used, even when the urine is instantaneously excreted, the pulp fiber having rapid absorption speed rapidly absorbs the urine immediately after the urination, and thereafter, the urine absorbed by the pulp fiber is gradually absorbed by the superabsorbent polymer and retained therein, whereby the backflow to the surface can be completely prevented.

By contrast, when the pulp fiber is more than 70 wt. % and the superabsorbent polymer is less than 30 wt. %, since the content ratio of the pulp fiber becomes higher, the water retentivity of the absorber 4 is low, and the backflow to the front sheet 3 after urination tends to occur. On the other hand, when the pulp fiber is less than 30 wt. % and the superabsorbent polymer is more than 70 wt. %, since the content ratio of the superabsorbent polymer becomes high, an initial absorption speed immediately after the urination is slow, the transfer of the urine from the front sheet 3 to the absorber 4 does not proceed smoothly, and the liquid residue tends to occur on the front sheet 3 immediately after the urination.

Furthermore, since the urine is surely absorbed and retained in the absorber immediately after the urination and the liquid residue is not caused in the front sheet, a diffusion range of the urine on the front sheet can be suppressed from expanding.

The absorber 4 is desirably surrounded by a wrapping sheet 5 such as crepe paper for shape retention and polymer powder retention.

(Intermediate Sheet)

When the front sheet 3 has many open holes 10, in order to prevent the pulp, polymer, adhesive or the like that constitute the absorber 4 from being exposed from the open holes 10, an intermediate sheet 6 is preferably provided between the front sheet 3 and the absorber 4. The intermediate sheet 6 also has a function of preventing the backflow from the absorber 4 and of making the skin contact during wearing soft due to the cushion effect. However, in a part where the open hole is not provided on the front sheet 3, the intermediate sheet 6 may be arranged, or may not be arranged. Furthermore, in the case of the front sheet 3 shown in FIG. 5, since the second sheet 23 is laminated on a surface on the absorber 4 side, the intermediate sheet 6 may not be further provided.

The intermediate sheet 6 may be formed into a single layer structure or may be formed into a two-layer structure by folding into a tube. The intermediate sheet 6 may be provided over an entire skin contact surface or may be provided only on a center in the width direction and on the intermediate part in the front-back direction (in particular, on a groin part).

A raw material of the intermediate sheet 6 may be one having liquid permeability but particularly preferably one having hydrophilicity. By combining the hydrophilic intermediate sheet 6 like this with a water repellent holed front sheet 3 of the present invention, the liquid permeability and backflow prevention performance of the front sheet 3 are remarkably improved. As the hydrophilic raw material like this, one having hydrophilicity in the raw material itself is used by using recycled fiber such as rayon, cupra, or the like, or natural fiber such as cotton or the like, or fiber provided with hydrophilicity by surface treating synthetic fiber that is for example olefin-based such as polyethylene or polypropylene, polyester-based, polyamide-based, or composite fibers thereof, copolymers thereof, or blend bodies thereof with a hydrophilizing agent may be used. Preferably, fiber obtained by mixing polyethylene and polypropylene may be used. As the fiber that constitutes the nonwoven fabric, any one of long fiber, short fiber, or mixtures thereof may be used. The fineness is set at about 2.0 to 7.0 dtex, preferably at about 4.0 to 6.0 dtex. As the intermediate sheet 6, any of known forms of nonwoven fabrics such as an air through nonwoven fabric, an air laid nonwoven fabric, a spun-bond nonwoven fabric or the like may be used, but the air through nonwoven fabric that does not degrade the air permeability may be preferably used.

Furthermore, in the case of the incontinence pad, as was described above, in many cases, it is continuously used until the second incontinence. Therefore, it is more preferable to use not a simple hydrophilic nonwoven fabric but to use a strongly hydrophilic or durable hydrophilic nonwoven fabric obtained by spraying a strongly hydrophilic agent and/or a durable hydrophilic agent on the nonwoven fabric. The basis weight of the strongly hydrophilic agent or durable hydrophilic agent may be set at 10 to 40 $g/m^2$, preferably at about 25 $g/m^2$. The basis weight of the intermediate sheet 6 is preferably set at 20 to 30 $g/m^2$.

In the front sheet 3, in order to prevent the liquid residue of the urine and to make a skin trouble such as irritation or rash during wearing difficult to occur, many open holes 10 that go through two sides are formed in a region that preferably included an excretion hole corresponding part H, is 15% or more of an absorber length in the product length direction, and is 50% or more of the absorber width in the product width direction. Therefore, the intermediate sheet 6 is arranged with a size that covers at least an entire surface of the open hole formation region. Specifically, the intermediate sheet 6 is preferably arranged with a size that is 9% or more of the size of the absorber 4 and that covers an entire surface of the open hole formation region.

The front sheet 3 is desirably adhered with a hot-melt adhesive because heat embossing cannot be adopted. The kind of the hot-melt adhesive is not limited, but an SBS (styrene-butadiene-styrene block copolymer)-based hot-melt adhesive is particularly desirable.

EXPLANATION OF REFERENCE NUMERALS

1/INCONTINENCE PAD
2/LIQUID-IMPERMEABLE BACK SHEET
3/FRONT SHEET
4/ABSORBER
5/WRAPPING SHEET
6/INTERMEDIATE SHEET
7/SIDE NONWOVEN FABRIC
8/THREAD-LIKE ELASTIC STRETCHABLE MEMBER
10/OPEN HOLES
11/VERTICAL LINE
12/HORIZONTAL LINE
20/FIRST PROTRUSTION PART LINE
21/SECOND RECESS PART LINE
22/PARTITION AREA
23/SECOND SHEET

The invention claimed is:

1. An absorbent article comprising an absorber interposed between a front sheet and a back sheet, wherein
the absorbent article is an incontinence pad for use with a medium or larger volume that absorbs 20 cc or a larger volume of urine;
the front sheet is formed by coating a water repellent at least at an excretion hole corresponding part on a spunlace nonwoven fabric made of 100 wt. % of cotton fiber and, on a skin facing surface side thereof, in a plan view, recess part lines of a diamond-shaped lattice pattern are formed from many first recess part lines that go along a predetermined inclination angle direction and are formed with a constant gap in the longitudinal direction of the absorbent article and many second recess part lines that go along an inclination angle direction obtained by reversing the first recess part lines in a width direction by a longitudinal direction line of the absorbent article and are formed with a constant gap in the longitudinal direction of the absorbent article, partition areas of a diamond-shaped lattice shape partitioned by these recess part lines are arranged adjacently in the longitudinal direction and the width direction of the absorbent article, and many open holes penetrating through two sides are formed at least at the excretion hole corresponding part; and
a longitudinal dimension S1, corresponding to the longitudinal direction of the absorbent article, and a transversal dimension S2, corresponding to the width direction of the absorbent article, of the partition areas of the diamond-shaped lattice shape are set at 5 to 20 mm, and the diamond-shaped lattice shape is formed longer in the width direction than in the longitudinal direction, such that the diamond-shaped lattice shape satisfies the following: the transversal dimension S2>the longitudinal direction S1,
on the absorber side of the front sheet, a second sheet made of a thermoplastic fiber is adhered thereto, and at the same time, the front sheet and the second sheet are bonded at the first recess part lines and second recess part lines by heat sealing of the second sheet, basis weights of the recess part lines and the basis weight of the partition area are formed at a substantially equal level, and the density of the recess part lines is formed higher than the density of the partition area.

2. The absorbent article according to claim 1, wherein the first recess part lines and second recess part lines are formed by any one of a continuous line or an intermittent line.

3. The absorbent article according to claim 2, wherein as the water repellent, glyceryl stearate is used.

4. The absorbent article according to claim 3, wherein the front sheet is made of degreased cotton fiber or non-degreased cotton fiber.

5. The absorbent article according to claim 2, wherein the front sheet is made of degreased cotton fiber or non-degreased cotton fiber.

6. The absorbent article according to claim 1, wherein as the water repellent, glyceryl stearate is used.

7. The absorbent article according to claim 6, wherein the front sheet is made of degreased cotton fiber or non-degreased cotton fiber.

8. The absorbent article according to claim 1, wherein the front sheet is made of degreased cotton fiber or non-degreased cotton fiber.

* * * * *